US00PP11609P

United States Patent [19]

Zaiger et al.

[11] Patent Number: Plant 11,609

[45] Date of Patent: Oct. 31, 2000

[54] INTERSPECIFIC TREE NAMED 'FLAVORITE'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 09/228,511

[22] Filed: Jan. 11, 1999

[51] Int. Cl.[7] ..... A01H 5/00

[52] U.S. Cl. ..... Plt./180; Plt./184

[58] Field of Search ..... Plt./180, 184, 186

*Primary Examiner*—Howard J. Locker
*Assistant Examiner*—Melissa L. Kimball

[57] ABSTRACT

A new and distinct variety of interspecific tree (*Prunus salicina*×*Prunus armeniaca*); the features of the tree and its fruit are characterized with the tree budded on Nemaguard rootstock, grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization. Its novelty consists of the following unique combination of desirable features that are outstanding in a new variety:

1. Fruit with excellent flavor and eating quality.
2. Fruit holding firm on the tree 12 to 15 days after maturity (shipping ripe).
3. Fruit with high soluble solids, averaging 20.1° Brix.
4. Fruit flavor being distinctively different, a blend between plum and apricot with a good balance between acid and sugar.
5. Heavy and regular bearer of fruit.
6. Relatively uniform ripening of fruit.
7. Vigorous semi-spreading growth of the tree.
8. Fruit with good handling and shipping quality.

1 Drawing Sheet

ORIGIN OF THE VARIETY

The present new and distinct variety of interspecific tree was originated by us in our experimental orchard located near Modesto, Calif., as a first generation cross between two selected seedlings with field identification numbers 16GG159 and 26GF10. The maternal parent 16GG159 originated from a cross of two selected seedlings 25GB924 and 4G1180. The seedling (25GB924) originated from a plum of unknown parentage crossed with a plumcot which originating from an open pollinated Red Beaut Plum (U.S. Plant Pat. No. 2,539) seed. The pollen parent (26GF10) originated from a cross of a selected seedling with field identification number 21GB794 with Royal Zee Plum (U.S. Plant Pat. No. 5,486). The selected seedling (21GB794) originated from a cross of a plumcot of unknown parentage with King David Plum (non-patented). A large group of these first generation seedlings, growing on their own root, were planted and maintained under close observation by us, during which time the present new interspecific variety exhibited the outstanding fruit characteristics described above and was selected for asexual propagation and commercialization.

ASEXUAL REPRODUCTION OF THE VARIETY

Asexual reproduction of the new and distinct variety of interspecific tree was by budding to Nemaguard rootstock, as performed by us in our experimental orchard located near Modesto, Calif., and shows that reproductions run true to the original tree and all characteristics of tree and the fruit are established and transmitted through succeeding asexual propagations.

SUMMARY OF THE VARIETY

The herein new and distinct variety of interspecific tree is of large size, vigorous, semi-spreading growth and a productive and regular bearer of medium size, firm, yellow flesh, freestone, fruit with excellent flavor and eating quality.

The fruit is further characterized by holding firm on the tree 12 to 15 days after maturity (shipping ripe) and having relatively uniform maturity throughout the tree. The fruit has a distinctive flavor, being a blend between apricot and plum with a lingering after taste. The firm flesh of the fruit has good storage and shipping quality. In comparison to the fruit of the interspecific tree Flavor King (U.S. Plant Pat. No. 8,026), the fruit of the new variety is approximately 30 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Tree pruned to 12 to 14 feet in height and 12 to 14 feet in width at maturity, primarily for economical harvesting of fruit.

*Vigor.*—Vigorous. Growth of 5 to 7 feet in first growing season. Pruned to 4 to 4½ feet during first dormant season to select primary scaffolds.

*Growth.*—Semi-spreading. Growth habit slightly similar to apricot tree growth, heavy crop load has tendency to spread width of tree.

*Productivity.*—Productive. Fruit set is 1½ to several times the amount of fruit desirable for crop load. Fruit is thinned and spaced to the desired number to produce marketable size fruit.

*Bearer.*—Regular. Has set crop load for 5 consecutive years.

*Density.*—Medium dense. Usually pruned to vase shape by removing small limbs from center of tree to increase amount of sunlight to the center of the tree, enhancing fruit color and Brix.

*Hardiness.*—Grown in USDA Hardiness Zone 9. Estimated chilling requirement to be 550 to 600 hours below 45° F.

Trunk:

*Size.*—Large.

*Texture.*—Shaggy.

*Color.*—Mustard brown to tobacco brown (5-E-6) to (5-F-6).

Branches:

*Size.*—Medium.

*Texture.*—Smooth to medium shaggy, varies with age of growth.

*Lenticels.*—Medium number. Large size.

*Color.*—Light brown to brown (5-D-7) to (5-E-8).

Leaves:

*Size.*—Medium to large. Average length 4½ inches. Average width 2 inches.

*Form.*—Oblanceolate. Pointed.

*Margin.*—Serrate.

*Thickness.*—Medium.

*Surface.*—Smooth.

*Petiole.*—Medium length. Average ⅞ inch.

*Glands.*—Globose. Number varies from 3 to 7. Average number 4. Small size.

*Color.*—Upper surface — spinach green to deep green (29-E-5) to (29-E-8). Lower surface — pea green to light green (29-D-5) to (29-D-8).

Flower buds:

*Size.*—Medium.

*Length.*—Medium.

*Form.*—Plump.

Flowers:

*Size.*—Medium. Average diameter 11/26 inch.

*Pollen.*—Present.

*Blooming period.*—Date of First Bloom Feb. 12, 1997. Date of Last Bloom Feb. 22, 1997. Varies slightly with climatic conditions.

*Color.*—White (1-A-1).

Fruit:

*Maturity when described.*—Firm ripe.

*Date of first picking.*—Jul. 6, 1997.

*Date of last picking.*—Jul. 11, 1997. Varies slightly with climatic conditions.

*Size.*—Medium. Average diameter axially 2⅛ to 2 3/16 inches. Average transversely in suture plane 2¼ to 2⅜ inches. Average 112 grams, varies from 108 to 117 grams.

*Form.*—Globose, slightly flattened between apex and base of fruit.

*Suture.*—Shallow, extends from base to apex.

*Ventral surface.*—Only slightly lipped, nearly rounded.

*Apex.*—Slightly retuse, nearly flat.

*Base.*—Retuse.

*Cavity.*—Rounded, slightly elongated in suture plane. Average depth ¼ inch. Average breadth ⅜ inch.

Flesh:

*Ripens.*—Nearly even, very slightly earlier near apex.

*Texture.*—Firm, meaty.

*Fibers.*—Few, very small, tender.

*Aroma.*—Very slight.

*Amygdalin.*—Undetected.

*Eating quality.*—Excellent, good balance between sugar and acid.

*Flavor.*—Excellent.

*Juice.*—Average 20.1° Brix. Moderate, sweet, mild, enhances flavor of flesh.

*Color.*—Apricot yellow to light orange (5-A-6) to (6-A-6). Red flesh near skin surface, Bordeaux red to brownish red (11-C-8) to (11-D-8) heavier near apex. Pit cavity — orange gray to brownish yellow (5-B-6) to (5-B-8).

Stem:

*Size.*—Medium. Average length 9/16 inch. Average width 3/32 inch.

*Color.*—Varies from light brown to oak brown (5-D-8) to (5-E-8).

Skin:

*Thickness.*—Medium.

*Texture.*—Medium, tenacious to the flesh.

*Down.*—Wanting.

*Bloom.*—Moderate amount.

*Tendency to crack.*—None.

*Color.*—Dark yellow to light orange (5-A-8) to (5-B-8) ground color. Overspread with Bordeaux red to garnet red (10-D-8) to (11-E-8) except in small areas, randomly spaced showing a speckling of yellow ground color.

Stone:

*Type.*—Freestone, on some fruit the fibers of the flesh adhere to stone along suture ridges.

*Size.*—Medium. Average length ¾ inch. Average width ¾ inch. Average thickness 13/32 inch.

*Form.*—Obovate.

*Base.*—Varies from straight to rounded.

*Apex.*—Acuminate, very small in size.

*Surface.*—Very lightly pitted throughout, two narrow long ridges on each side of suture extending from base to apex. Some stones have one or more small, short, ridges running from base toward apex.

*Sides.*—Equal to unequal, some stones have one side extending outward farther from suture plane.

*Tendency to split.*—None.

*Color.*—Light brown to caramel brown (6-B-5) to (6-C-6).

Use: Dessert. Market — local and long distance.

Keeping quality: Good. Fruit held firm in storage 3 weeks with no internal breakdown.

Shipping quality: Good. The firm flesh had minimal bruising or skin scarring during packing shipping trials.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, which is of large size, vigorous, semi-spreading growth and being a productive and regular bearer of medium size fruit with excellent flavor and eating quality; the fruit is further characterized by holding firm on the tree 12 to 15 days after maturity, having good storage and shipping quality and, in comparison to the interspecific tree Flavor King (U.S. Plant Pat. No. 8,026), the fruit of the new variety is approximately 30 days later in maturity.

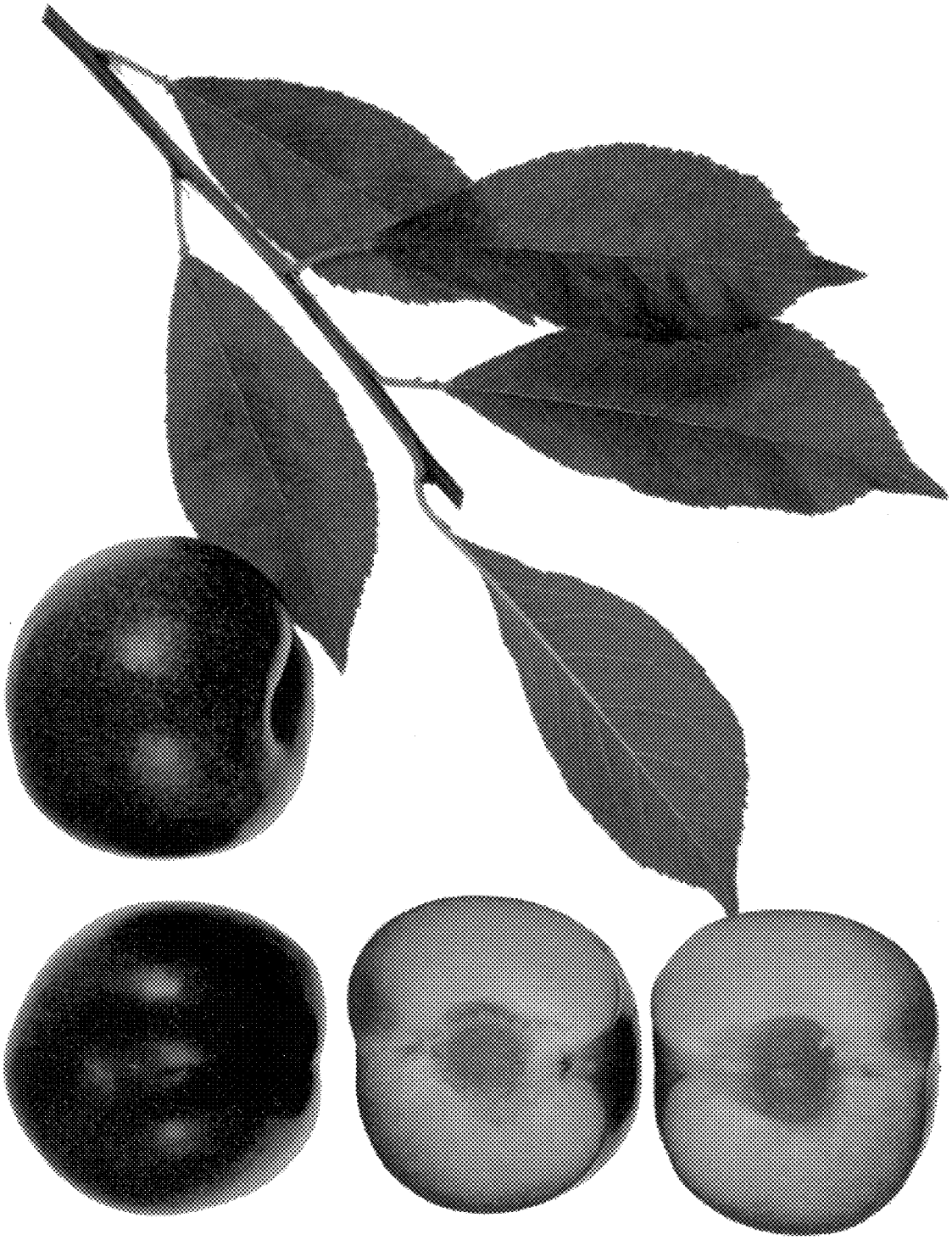

* * * * *